United States Patent
Lee

(10) Patent No.: US 11,807,885 B2
(45) Date of Patent: Nov. 7, 2023

(54) BLACK GARLIC EXTRACT FROM SEPARATED GARLIC BULBS AND PREPARATION METHOD THEREOF

(71) Applicant: HAANONG FOODS. CO., LTD., Pocheon-si (KR)

(72) Inventor: Jung Bin Lee, Yongin-si (KR)

(73) Assignee: HAANONG FOODS. CO., LTD., Pocheon-si (KR)

(*) Notice: Subject to any disclaimer, the term of this patent is extended or adjusted under 35 U.S.C. 154(b) by 226 days.

(21) Appl. No.: 17/128,473

(22) Filed: Dec. 21, 2020

(65) Prior Publication Data

US 2021/0198705 A1 Jul. 1, 2021

(30) Foreign Application Priority Data

Dec. 30, 2019 (KR) .......................... 10-2019-0177879

(51) Int. Cl.
*C12P 13/12* (2006.01)
*A61K 36/8962* (2006.01)
*C12P 19/14* (2006.01)

(52) U.S. Cl.
CPC .......... *C12P 13/12* (2013.01); *A61K 36/8962* (2013.01); *C12P 19/14* (2013.01); *A61K 2236/31* (2013.01); *A61K 2236/37* (2013.01)

(58) Field of Classification Search
None
See application file for complete search history.

(56) References Cited

FOREIGN PATENT DOCUMENTS

| KR | 10-0797915 B1 | 1/2008 |
|---|---|---|
| KR | 10-0888692 B1 | 3/2009 |
| KR | 10-0895615 B1 | 5/2009 |
| KR | 10-0959513 B1 | 5/2010 |
| KR | 10-2010-0097348 A | 9/2010 |
| KR | 10-0983213 B1 | 9/2010 |
| KR | 10-0987233 B1 | 10/2010 |
| KR | 10-1065160 B1 | 9/2011 |
| KR | 10-2012-0018505 A | 3/2012 |
| KR | 10-1281510 B1 | 7/2013 |
| KR | 10-1307090 B1 | 9/2013 |
| KR | 10-2013-0140293 A | 12/2013 |
| KR | 10-1401956 B1 | 6/2014 |
| KR | 10-1418843 B1 | 7/2014 |
| KR | 10-1785348 B1 | 10/2017 |
| KR | 10-1913096 B1 | 10/2018 |

OTHER PUBLICATIONS

Google Patents English translation of JP4080507B2 (issued Apr. 23, 2008). (Year: 2008).*
CN108125238A (published Jun. 18, 2018; translation from Google Patents) (Year: 2018).*

* cited by examiner

*Primary Examiner* — Michael Barker
(74) *Attorney, Agent, or Firm* — Carol A. Marmo; Eckert Seamans Cherin & Mellott LLC

(57) ABSTRACT

The present invention relates to a novel black garlic extract using garlic bulbs separated into six bulbs as a raw material instead of conventional whole garlic and a preparation method thereof. There is an excellent effect of providing a novel black garlic extract with various functionalities of high sweetness and high viscosity and improved flavor and reddish brown color as well as induce high-concentration conversion of 10 times or more to a S-allyl-cysteine compound in which a functional ingredient of raw garlic having antioxidation, reduction in blood cholesterol, improved liver function, and enhanced blood pressure is present in a small amount of 10 ppm or less by maximizing conversion of starch into reducing sugar for most preferably 15 days in a 90% to 100% saturated steam state and a liquefied enzymatic action temperature of 75° C. to 80° C. or lower without separate enzyme addition, and optimizing the action of proteases.

1 Claim, 2 Drawing Sheets

BLACK GARLIC EXTRACT FROM SEPARATED GARLIC BULBS AND PREPARATION METHOD THEREOF

CROSS-REFERENCE TO RELATED APPLICATIONS

This patent application claims the benefit of priority from Korean Patent Application No. 10-2019-0177879, entitled "Novel Black Garlic Extract From Separated Garlic Bulbs and Preparation Method Thereof", filed on Dec. 30, 2019, the contents of which are incorporated by reference herein in their entirety.

BACKGROUND OF THE INVENTION

Technical Field

The present invention relates to a novel black garlic extract from separated garlic bulb as a raw material and a preparation method thereof, and more specifically, to provide a high-viscosity reddish brown garlic extract with improved sweetness and flavor characterized by using and fermenting/ripening garlic separated into garlic bulbs as a raw material by adopting high temperature and high humidity conditions of 75° C. to 80° C. as a liquefied enzymatic action temperature and 95% to 100%.

Background Art

Garlic (*Allium Sativum* L.) is a scale-stem vegetable belonging to the genus *Allium* of the Liliaceae family, and is one of representative foods that improve the taste and health of food. Garlic is shipped from June to August, some thereof has been used as raw vegetables, and the rest thereof is stored until the following spring. The garlic is one of representative agricultural products in which significant nutritional losses are incurred due to drying, spoilage, and germination during ripening and price fluctuates are severe according to crop conditions. Garlic, which has a strong odor, has been used in spices and pickles in various foods as an essential seasoning for our diet. In addition, recently, it has been found that garlic is health-oriented food as well as cholesterol reduction, anti-aging, anti-cancer, and various antibacterial effects. In Sheo (1999), it was reported that in an antibacterial action experiment of garlic, onion, ginger, and red pepper juice, garlic showed the greatest antimicrobial activity compared to other samples. In Nagai et al. (2000), it was reported that while garlic's pharmacological function against heart diseases, headaches, tumors, parasites, etc., such that there is a significant effect on influenza virus infection defense was found when about 10 bulbs of garlic was taken, the garlic tended to be used as materials for health supplements and medicines.

The biggest problem in garlic processing has been indicated with oxidation, discoloration, and changes in flavor by enzymes. The discoloration of garlic may be represented by browning and greening. The greening is mainly caused by processing garlic ripened at a low temperature, and as the cause, it has been reported that when garlic of which a dormant period has elapsed was influenced by a physical action, metabolism has been suppressed, and then alliinase acted due to sudden external influences such as temperature rise, light, and metal, and as a result, a pigment precursor reacted with carbohydrates contained in garlic to cause greening. Browning in processed garlic products is classified into non-enzymatic browning such as caramel reaction, mailard reaction, etc. and enzymatic browning by polyphenoloxidase (PPO), and at a high temperature during garlic processing, the non-enzymatic browning reaction by the reaction between peptides and amino groups of amino acids and sugars mainly occurs at a high temperature.

The most traditional method to remove the odor of garlic is steaming or roasting garlic. It has been known that the garlic is roasted, its flavor becomes sweet and a pungent odor becomes soft, and when the garlic is freeze-dried, the flavor becomes relatively mild compared to raw garlic, and the retention rate of functional ingredients is significantly high as compared to another processing method. Recently, it has been tried to develop a new type of processed product with functionality using this browning reaction of garlic, and when whole garlic is ripened for a certain period in a high-temperature thermostat, even the inside of the garlic turns black by ingredients of garlic itself, enzymes, etc., which is called black garlic in the market. Characteristically, the black garlic has a dark brown color and decreased spicy taste of garlic, while has increased viscosity, is harmonized in sweet and sour tastes, and has softer flavor than raw garlic, and thus, the black garlic is emerging as a material capable of manufacturing various processed foods. However, the preparation method of the black garlic is not unified, and thus, the overall quality, including flavor, varies depending on a manufacturer. Therefore, efforts are being made to improve a facility aspect for solving this problem.

On the other hand, as the representative functionality of the black garlic, antioxidation, reduction in body fat, immunity enhancement, reduction in cholesterol, improvement of liver function, etc. have been reported. The black garlic extract has been shown to increase its functionality due to an increase in the content of S-allyl-cysteine having an anti-cancer effect, and the like.

A conventional method for preparing a black garlic extract has generally been performed by fermenting, ripening, and extracting whole garlic as it is for about 1 month or boiling or roasting the whole garlic and then adding water to prepare an extract.

Meanwhile, up to now, Korean Patent Registration No. 10-1401956 has been disclosed as a factory-scale method for preparing a black garlic extract. However, Korean Patent Registration No. 10-1401956 relates to a black garlic extract and a preparation method thereof characterized in that whole garlic is directly juiced, added with purified water, heated at 90° C. to 100° C. for 3 hours, and then cooled after Allinase is inactivated to remove a spicy component of garlic, and the heated garlic juice is added with pectinase as a softening enzyme, carbohydrase as a saccarifying enzyme, and flavozyme as protease in sequence to be enzymatically decomposed and then promote the browning at 90° C. to 100° C. There is a disadvantage in that the final product has low palatability due to the color of black or dark brown by complex treatment of various enzymes in three stages.

Alternatively, as the method for preparing the black garlic extract, Korean Patent Registration No. 10-1418843 has been disclosed. However, this is a method of preparing animal feed directly from garlic, and there is disclosed a conventional method for preparing an extract in which a black garlic extract and a black garlic bark are separated from black garlic to be configured as a black garlic extract coating layer containing agar or dextrin, wherein the roots of black garlic are cut, white whole garlic is added into a steamer and rapidly steamed at 90° C. for 200 hours, i.e., about 7 to 8 days, and then the black garlic extract is juiced and the black garlic bark is separated and collected.

In addition, in Korean Patent Registration No. 10-1913096, there is disclosed a preparation method of Haesintang containing a black garlic extract, and in Korean Patent Registration No. 10-1785348, there is disclosed a preparation method of a black garlic extract. In the former, disclosed is a black garlic extract prepared by hot-streaming all of six bulbs of peeled whole garlic in a rice cooker, drying the hot-steamed garlic for 7 to 13 days again, and then heating and extracting the dried garlic at 100° C./5 to 10 hours. In the latter, disclosed is an extraction method of naturally drying peeled whole garlic and raw maca, adding the dried mixture with purified water in a water bath, hot-heating and streaming the mixture at 90° C. to 100° C./20 to 30 minutes, and then ripening the mixture under reduced pressure and adding purified water.

However, even in any document, there is not disclosed or implied at all a preparation method of a garlic extract with improved flavor and sweetness and increased redness and viscosity of a black garlic extract by separating whole garlic into garlic bulbs to be used as a raw material of a garlic extract or fermenting/ripening the garlic bulbs under conditions of a medium-high temperature and a saturated steam state with only an enzyme contained in the garlic without adding an enzyme, particularly, selecting the liquefied enzymatic action temperature and humidity of 75° C. to 80° C./95% to 100%, most preferably autolysis for 15 days.

PRIOR ARTS

Patent Documents

Korean Patent Publication No. 10-2011-0053212,
Korean Patent Publication No. 10-2012-0018505,
Korean Patent Publication No. 10-2010-0097348,
Korean Patent Publication No. 10-2013-0140293,
Korean Patent Registration No. 10-895615,
Korean Patent Registration No. 10-797915,
Korean Patent Registration No. 10-959513,
Korean Patent Publication No. 10-2012-0113323,
Korean Patent Registration No. 10-1401956,
Korean Patent Registration No. 10-1065160,
Korean Patent Publication No. 10-2009-0082533,
Korean Patent Registration No. 10-888692, and
Korean Patent Registration No. 10-983213

SUMMARY OF THE INVENTION

In one aspect, the invention provides a method of preparing a black garlic extract comprising the steps of: (a) separating whole garlic into garlic bulbs and washing the garlic bulbs; (b) fermenting and ripening the washed garlic bulbs obtained in step (a) as a raw material in a saturated state of humidity of 90% to 100% and under a temperature condition of 75° C. to 80° C. as a liquefied enzymatic action temperature or less; (c) first juicing the ferment-ripened material obtained in step (b) to obtain an extract; (d) further fermenting and ripening the remaining raw material after the juicing in step (c) under a 80° C. to 90° C./90% to 100% saturated state for 2 to 3 days by adding water and then second juicing the ferment-ripened material and mixing the second juiced material with the first juiced extract; and heating and concentrating the mixed juiced extract obtained in step (d) at 100° C. to inactivate an enzyme.

In another aspect, the invention provides a high-viscosity reddish brown black garlic extract prepared according to the foregoing method.

DETAILED DESCRIPTION OF THE PREFERRED EMBODIMENTS

Technical Problem

Therefore, an object of the present invention is to provide a black garlic extract and a preparation method thereof with improved sweetness and flavor and enhanced redness and viscosity by penetrating heat conduction and saturated water uniformly rather than using whole garlic by physically using garlic bulbs while applying a humidity condition in a hot saturated state for at least 2 weeks in an optimal condition of 75° C. to 80° C./95% to 100% of a liquefied enzymatic reaction for a carbohydrate ingredients constituting garlic.

Technical Solution

An object of the present invention is achieved by preparing a black garlic extract comprising the steps of (a) screening whole garlic and separating and washing garlic bulbs from the whole garlic; (b) fermenting and ripening the washed garlic bulbs obtained above in a saturated state of 95% to 100%, a medium-high temperature of 75° C. to 80° C. as a liquefied enzymatic action temperature, for 2 to 3 weeks, most preferably 15 days, instead of conventional conditions of ultra-high temperature of 90° C. to 100° C. and low humidity of 35% to 60% or less; (c) first juicing the ferment-ripened material obtained in step (b) to obtain an extract; (d) further fermenting and ripening the remaining raw material after the juicing in step (c) under 80° C. to 90° C./saturated steam conditions for 2 to 3 days and then second juicing the ferment-ripened material and mixing the second juiced material with the first juiced extract; and heating and concentrating the mixed juiced extract obtained in step (d) at 100° C. for 30 minutes to inactivate an enzyme, and evaluating its palatability and functionality.

Advantageous Effects

According to the present invention, not only there is an effect of providing a novel black garlic extract with a high-viscosity reddish-brown color and improved sweetness and flavor which has never existed so far, but also there is an excellent effect of providing a food composition of a new material with improved various palatability and functionalities at the same time by using the novel black garlic extract as described above.

MODES OF THE INVENTION

Figure 1:
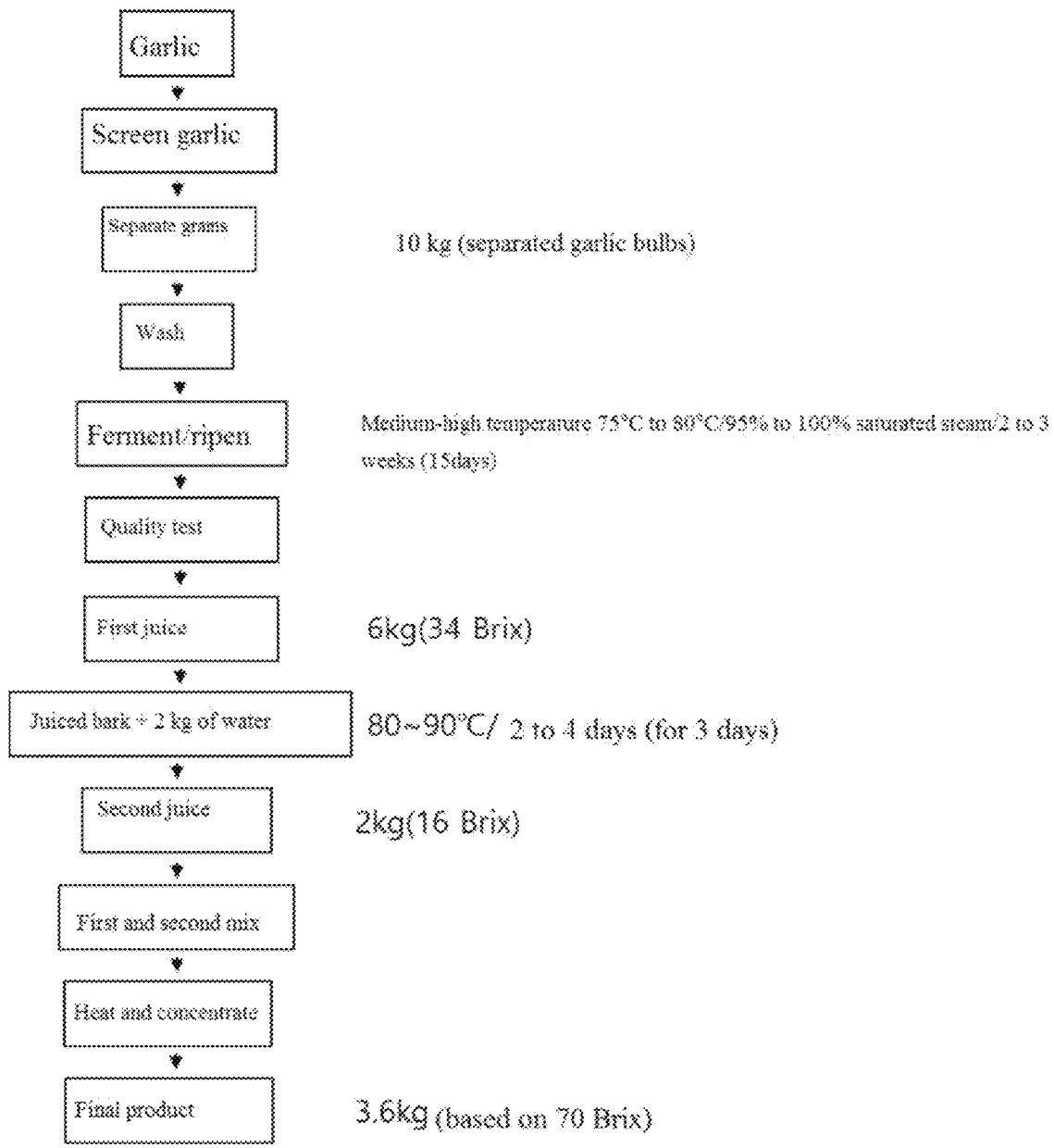
FIG. 1 is a diagram illustrating a process of preparing a novel black garlic extract as an embodiment of the present invention.

Hereinafter, the most preferred embodiment of the present invention has been described in more detail with reference to the accompanying FIG. 1, but the following Examples just provide the most preferred technical details for those skilled in the art to easily implement the present invention, but the present invention are not limited to only Examples of the present invention. It goes without saying that a change in a type of liquefied enzyme, a simple change in temperature and humidity for the enzyme treatment, etc. are included to the scope of the present invention.

EXAMPLES

Example 1

Preparation of High Viscosity/Reddish Brown Garlic Extract of the Present Invention 11 kg of 6 bulbs of raw garlic was prepared, a root portion was cut, and then white whole garlic was put into a cylindrical separator for separating grains to be separated into garlic bulbs and washed to obtain 10 kg of garlic bulbs.

The entire garlic bulbs washed above were put in a stainless steel steamer and autolyzed and then fermented and ripened at 80° C. or less as an optimum activity temperature of a liquefied enzyme, most preferably 75° C. in a saturated steam state of 95% or more for at least 2 weeks, most preferably 15 days.

At this time, it was confirmed that functional substances such as S-allyl-cysteine present in the raw garlic cells were activated, and autolysis in which starch was saccharified and liquefied by various sulfur-containing compounds and various carbohydrase enzymes was induced by the action of protease such as glutamyl transpeptidase, etc.

In the Example of the present invention, unlike known prior arts, while raw garlic was autolyzed at 80° C. or less, reducing sugar and amino acids converted directly in the cells of garlic were combined to induce the garlic to be changed to a brown color as a result of the Millard reaction. At the same time, the activation of a red-based natural red pigment contained in the bark of 6 bulbs of garlic was induced to be maximized, and a final ferment-ripened material had a reddish brown color (see FIG. 2).

According to the Example of fermenting and ripening the garlic at 80° C. or less in the saturated steam state of the present invention, there is also a feature in that the production of Allcine, a spicy ingredient, is appropriately induced by minimizing the inhibition of Allinase present in garlic cells.

Further, according to the present invention, it was characterized that the garlic bulbs were fermented and ripened at 80° C. or less in the saturated steam state to induce fermenting and ripening for 15 days naturally by various proteases such as glutamyl transpeptidase present in cells in the garlic, thereby inducing and converting an increase in content of a S-allyl-cysteine (SAC) compound, which was a functional substance of garlic. It has been known that this ingredient was present in a trace amount of 10 ppm or less in raw garlic.

Figure 2:
FIG. 2 is a photograph of high-viscosity reddish-brown black garlic with improved reducing sugar content and other functionalities prepared according to the present invention.

According to the present invention, it was characterized that under a temperature condition of 80° C. or less in a saturated steam state of 90% or more, the activation of various liquefied enzymes such as α-amylase derived from 6 bulbs of raw garlic was suppressed as much as possible to suppress the conversion of oligosaccharides with neutralization of 7 or more as a starch ingredient and increase the contents of glucose and maltose as a whole preferably at the beginning of ferment-ripening, thereby enhancing both high viscosity and sweetness (FIG. 2).

According to the results of multiple experiments by the present inventors, in a saturated steam state of 90% or more and 100% and under a reaction temperature conduction of a liquefied enzyme in garlic cells, that is, 80° C. or less, rapid saccharification for at least 2 weeks, most preferably 15 days was most suitable for maximizing the viscosity and sweet ingredients of the autolyzed product. On the other hand, within 2 weeks at 75° C. to 80° C., sufficient saccharification was not made, resulting in lowered sweetness and low redness. At 2 weeks or more, a large amount of olygosaccharides was produced by the action of the liquefied enzyme, resulting in a decrease in the viscosity of the final garlic extract product, but an increase in browning degree.

As described above, after a quality test of a sample subjected to fermenting/ripening of the garlic bulbs was completed, the garlic bulbs were put in a juicer and first juiced to obtain 6 kg of a black garlic extract of 34 Brix (stored separately). Then, the remaining juiced bark after first juicing was added with 2 L of washing water, and then put in a steamer and second fermented/ripened for 2 to 4 days at 80° C. to 90° C. of an action temperature or more of the liquefied enzyme, and then second juiced to obtain 3 kg of a black garlic extract of 16 Brix. 6 kg of the first black garlic extract (34 Brix) obtained above and a juiced bark separately therefrom were added with 2 kg of water and then put in a steamer so that a liquefied enzyme was applied, additionally fermented and ripened at 80° C. to 90° C./for 2 to 4 hours, and the remaining starch was converted into oligosaccharides. Thereafter, 3 kg of a black garlic extract (16 Brix) obtained by second juicing was mixed with the first juice and then heated and concentrated at 100° C. to inactivate all of the enzymes and obtain about 3.6 kg of a reddish brown garlic extract (70 Brix) of the present invention.

As described above, the saccharification enzymes act first to obtain a first extract with relatively high viscosity and high redness and then the liquefied enzymes act again to obtain a second extract with relatively low viscosity and high brown degree. The heat-concentrated extract of the mixed extract has a reddish-brown color with excellent functionality and improved palatability.

This was confirmed by the following experiments according to Examples 2 to 3 and Comparative Examples 1 to 3 involving separate enzyme treatment under conditions different from the most preferred Example 1 of the present invention.

Experimental Example 1

Experimental Plan for Selecting Optimal Fermenting/Ripening Conditions (Temperature and Humidity) and Time of Garlic Bulbs In order to select optimal fermenting/ripening conditions (temperature and humidity) and time of the garlic bulbs according to the present invention, an experiment plan as shown in Table 1 was established and experimented. The experimental results were shown in Table 2.

TABLE 1

Experiment scheme of selecting optimal fermenting/ripening (autolysis) temperature and humidity of garlic bulbs

| Classification | Humidity (%) | Temperature (° C.) | Treatment time | Whether to add separate enzyme |
|---|---|---|---|---|
| Example 1 | 90 | 70 | 15 days | X |
| Example 2 | 95 | 75 | 15 days | X |
| Example 3 | 100 | 80 | 15 days | X |
| Comparative Example 1 | 30 | 45/70 | 16 h/8 h | Rapidase C80 MAX 1% + Flavozyme 1% |
| Comparative Example 2 | 70 | 50/75 | 8 h/7 h | Equal |
| Comparative Example 3 | 100 | 60/80 | 6 h/6 h | Equal |

As a result of the experiment, the content of reducing sugar and the content of SAC were shown in Table 2 below.

TABLE 2

Contents of reducing sugar and SAC as result of bioconversion

| Classification | Content of reducing sugar (%) | Content of SAC (μg/g) | Viscosity (cp) |
|---|---|---|---|
| Example 1 | 3.24 | 198.4 | <40,000 |
| Example 2 | 4.42 | 212.3 | <70,000 |
| Example 3 | 4.13 | 182.4 | <50,000 |
| Comparative Example 1 | 0.83/0.27 | 97.0/52.2 | <3,200 |
| Comparative Example 2 | 0.42/0.17 | 32.1/48.3 | <1,700 |
| Comparative Example 3 | 0.11/0.014 | 21.2/30.2 | <1.2 |

According to the experimental results, in Example 2, which was fermented and ripened for 15 days at 95%/75° C. of saturated humidity of the present invention, the content of reducing sugar was the highest at 4.42%, and the sweetness was maximized. Therefore, it was suggested that the viscosity (cp) also showed a maximum of 70,000 or more, and the content of SAC was also maximized to be useful as an additive for various food materials.

Experimental Example 2

Results of Sensory Test for Black Garlic Extract of the Present Invention

The black garlic extract product manufactured according to Example of the present invention was compared with general commercial black garlic extract products manufactured by other companies K and N. The total number of sensory test panels was randomly selected to 10 persons (5 men and 5 women, respectively), and a sensory test was performed. For the test, a 5-point scaling method was used, and 1 point: worst, 2 points: bad, 3 points: normal, 4 points: good, and 5 points: very good were evaluated, and an average value thereof was indicated (Table 3).

TABLE 3

Sensory test results of black garlic extract

| Classification | Product of present invention | K company's product (1) | N company's product (2) |
|---|---|---|---|
| Appearance | 3.6 | 2.8 | 2.6 |
| Color | 3.6 | 3.0 | 2.6 |
| Flavor | 4.2 | 3.2 | 3.0 |
| Taste | 4.4 | 3.6 | 2.4 |
| Physical properties | 3.6 | 3.0 | 2.6 |
| Overall preference | 4.4 | 3.1 | 2.7 |

As can be seen from the experimental results, the black garlic product of the present invention is black, has a dark brown color compared to a low-viscosity K company's product, and has a reddish brown color compared to a low viscosity N company's product, and has a relatively high content of reducing sugar and high viscosity. Thus, the best results were obtained not only in appearance and color, but also in flavor and physical properties. It also showed the most outstanding excellence in the overall preference.

Experimental Example 3

Experimental Results Using Whole Garlic and Garlic Bulbs

The present inventors prepared 11 kg of 6 bulbs of garlic (whole garlic) as a raw material and finally obtained about 3.1 kg (65 Brix) of a black garlic extract through the same conditions, procedures and processes (Experimental Example 4) as in Example 2 using the garlic bulbs raw material as a starting material. The content (%) of reducing sugar, the content (μg/g) of S-allyl-cysteine, and the viscosity (cp) of the extract converted through the final fermenting/ripening process were as shown in Table 4 below.

TABLE 4

Comparison of bioconversion results between whole garlic and separated garlic bulbs

| Classification | Separated garlic bulbs (Example 2) | Whole garlic (Example 4) | Note |
|---|---|---|---|
| Reducing sugar (%) | 4.42 | 2.84 | |
| Content of SAC (μg/g) | 212.3 | 122.1 | |
| Viscosity (cp) | <70,000 | <54,000 | |

As a result of the experiment, compared to the method of preparing the black garlic extract using whole garlic directly as a raw material, in the method of preparing the black garlic extract through the steps of screening whole garlic and separating garlic bulbs from the whole garlic and washing the garlic bulbs, the fermenting/ripening time was shortened and the decomposition time of cellulose or hemicellulose of the fibrous bark was saved. In addition, under a saturated humidity condition of 95% or higher and a liquefied enzymatic action temperature of 80° C. or less, first, the saccharification of starch by carbohydrase was rapidly proceeded to increase the content of reducing sugar and the viscosity, and further increase the content of S-allyl-cysteine (SAC) by rapid autolysis of proteases. It was considered that the whole garlic had a relatively high content of fiber constituting the bark compared to the garlic bulbs, and thus, the results were obtained. The present inventors have determined that the black garlic extract needs to be prepared using the garlic bulbs.

The invention claimed is:

1. A method of preparing a black garlic extract comprising the steps of:
   (a) separating whole garlic into garlic bulbs and washing the garlic bulbs to obtain washed garlic bulbs;
   (b) fermenting and ripening the washed garlic bulbs obtained in step (a) as a raw material in a saturated state of humidity of 96% to 100% and under a medium-high temperature condition of 76° C. to 80° C. as a liquefied enzymatic action temperature, for at least two weeks to obtain a first ferment-ripened material;
   (c) first juicing the first ferment-ripened material obtained in step (b) to obtain a first juiced extract and remaining raw material;
   (d) further fermenting and ripening the remaining raw material after the first juicing in step (c) under a 80° C. to 90° C./96% to 100% saturated state for 2 to 3 days by adding water to obtain a second ferment-ripened material and then second juicing the second ferment-ripened material to obtain a second juiced material and mixing the second juiced material with the first juiced extract to obtain a mixed juiced extract; and heating and concentrating the mixed juiced extract obtained in step (d) at 100° C. to inactivate an enzyme, resulting in a black garlic extract.

\* \* \* \* \*